United States Patent [19]

Durvasula

[11] Patent Number: 4,577,034

[45] Date of Patent: Mar. 18, 1986

[54] AUTOXIDATION OF BIS(ORTHO DIALKYL-PHENOXY)BENZOPHENONES

[75] Inventor: Visweswara R. Durvasula, Cheshire, Conn.

[73] Assignee: The Dow Chemical Company, Midland, Mich.

[21] Appl. No.: 701,835

[22] Filed: Feb. 14, 1985

[51] Int. Cl.$^4$ ............................................ C07D 307/89
[52] U.S. Cl. ...................................... 549/241; 568/333
[58] Field of Search ............................................ 549/241

[56] References Cited

U.S. PATENT DOCUMENTS

| | | | |
|---|---|---|---|
| 2,833,816 | 5/1958 | Saffer et al. | 562/421 X |
| 3,652,598 | 3/1972 | Broadhead | 549/242 |
| 3,833,546 | 9/1974 | Takekoshi et al. | 528/188 |
| 4,526,984 | 7/1985 | Durvasula | 549/241 |

OTHER PUBLICATIONS

Paparinska et al., Khim Tekhnol Khim 1974, 2, 86-97 (Chemical Abstracts, 82, 124995r, 1975).

*Primary Examiner*—Richard L. Raymond
*Attorney, Agent, or Firm*—J. S. Rose

[57] ABSTRACT

A method is described for autoxidizing a novel class of bis(ortho dialkyl-phenoxy)benzophenones directly to their corresponding dianhydrides. The method comprises autoxidizing the benzophenones in a solution of an aliphatic monocarboxylic acid having 3 to 8 carbon atoms with oxygen in the presence of a heavy metal oxidation catalyst and a promoter at a temperature of at least about 120° C. to form the dianhydride.

The dianhydrides are used in the preparation of organic high temperature polymers such as polyetherimides.

9 Claims, No Drawings

AUTOXIDATION OF BIS(ORTHO DIALKYL-PHENOXY)BENZOPHENONES

FIELD OF THE INVENTION

This invention relates to the autoxidation of ortho dialkyl substituted aromatic compounds and is more particularly concerned with the autoxidation of certain ortho dialkyl substituted phenoxy benzophenones and novel precursors therefor.

DESCRIPTION OF THE PRIOR ART

The autoxidation of dialkyl substituted aromatic compounds to carboxylic acid products in aliphatic carboxylic acid solutions using heavy metal oxidation catalysts and promoters is well known, for example, see U.S. Pat. No. 2833816. When the reference procedure is employed with ortho dialkyl substituted aromatics the desired carboxylic acids are obtained in low yields only. The oxidation of the first alkyl group to the carboxylic acid group goes readily but the result is the deactivation of the adjacent alkyl group towards autoxidation.

An added complication arises with ortho dialkyl substituted aromatics when there are two or more such aromatic rings joined by a linking radical such as methylene, carbonyl, sulfonyl, or ether. Generally speaking, there is an even greater tendency towards lower product yields when such compounds are subjected to prior art autoxidation procedures. For example, Broadhead in U.S. Pat. No. 3,652,598 discloses the oxidation of various 2,2'-, 3,3'- and 3,3', 4,4'-tetraalkyldiphenylmethanes to the corresponding tetracarboxylic acids. Product mixtures are obtained which contain mono-, di-, tri-, and tetracarboxylic acids. Accordingly, the yield of desired tetracarboxylic acid product is low and its isolation and purification from the complex reaction mixtures becomes complicated.

Paparinska et al, Khim Tekhnol Khim 1974, 2, 86–97 (Chem. Abstracts 82, 124995r, 1975) have reported the cobalt acetate-sodium bromide catalyzed autoxidation of 3,3', 4,4'-tetramethyldiphenyl ether to the corresponding tetracarboxylic acid in only a 40 to 50 percent yield.

When products such as the tetracarboxylic acids described by Broadhead and Paparinska et al cited supra are desired, they are generally preferred in the form of the dianhydride. Obviously, this requires the conversion of the tetracid to the dianhydride form.

Bis(dicarboxyphenoxy)benzophenone dianhydrides have been prepared not by autoxidation procedures but by the condensation of nitro-substituted ortho-dicyanobenzenes with the di-alkali metal salt of a dihydric phenol and subsequent hydrolysis of the condensed product to the tetracarboxylic acid followed by dehydration to dianhydride (see U.S. Pat. No. 3,833,546). Alternatively, the dianhydrides have been prepared using the above method but starting with the N-substituted nitrophthalimide (vide supra).

In copending application Ser. No. 665,905 filed Oct. 29, 1984, now U.S. Pat. No. 4,526,984, a novel process is disclosed for the autoxidation of a particular group of ortho dialkyl substituted aromatic ether compounds to their dianhydrides in high yields. This method calls for a two-step autoxidation first in the presence of a carboxylic acid followed by continued oxidation in a particular carboxylic acid anhydride.

I have now discovered that a particular class of ortho dialkyl substituted phenoxy benzophenones can be autoxidized directly to their corresponding dianhydride form in high yields in a process which does not require the use of an anhydride.

SUMMARY OF THE INVENTION

This invention comprises a method for converting bis(ortho dialkyl-phenoxy)benzophenones having the formula (I) (see FORMULA CHART) to the corresponding dianhydrides having the formula (II) wherein $R$, $R_1$, $R_2$, and $R_3$ are independently selected from linear lower alkyl, said method comprising autoxidizing said benzopheones (I) in a solution of an aliphatic monocarboxylic acid having 3 to 8 carbon atoms with oxygen in the presence of a heavy metal oxidation catalyst and a promoter and at a temperature of at least about 120° C. to form said dianhydride (II).

It will be understood by those skilled in the art that the present method also contemplates the use of those bis(ortho dialkyl-phenoxy)benzophenones wherein the aromatic rings can be additionally substituted by inert groups not oxidizable under the present autoxidation conditions. Typical of such groups are halogen (flourine, chlorine, bromine, iodine), alkoxy (such as methoxy, ethoxy), and the like.

This invention also comprises said benzophenones of formula (I).

The term "linear lower alkyl" means alkyl having from 1 to 8 carbon atoms, inclusive, such as methyl, ethyl, propyl, butyl, amyl, hexyl, heptyl, and octyl.

The dianhydrides (II) obtained from the present method are used as intermediates in the preparation of various polymers but find their principal utility in the preparation of high temperature resistant polyetherimides of the type disclosed in U.S. Pat. No. 3,833,546 cited supra.

DETAILED DESCRIPTION OF THE INVENTION

The process in accordance with the present invention is characterized by the surprising feature of providing directly, and, in high yields, the dianhydrides (II) under reaction conditions which the prior art contrarily teaches would produce a mixture of carboxylic acid products including the mono-, di-, tri-, and tetracarboxylic acids.

The autoxidation is carried out using procedures analogous to the prior art methods cited supra. That is to say, the compounds (I) are autoxidized in a solution comprising an aliphatic monocarboxylic acid set forth above in the presence of any type of heavy metal oxidation catalyst known in the art along with a promoter to form the dianhydride products. The reaction can be carried out in any suitable reaction vessel including glassware and sealed autoclaves capable of withstanding high pressures. For typical methods, including reaction procedures, oxidizing techniques including catalysts, promoters, and the like, the disclosure of U.S. Pat. No. 2,833,816 cited supra is incorporated herein by reference.

The aliphatic monocarboxylic acid solvent employed is defined above as having 3 to 8 carbon atoms, and, preferably, has 3 or 4 carbon atoms. Illustrative of these carboxylic acid solvents are propionic, butyric, isobutyric, valeric, caproic, heptylic, caprylic, and the like acids. Preferred are propionic, and butyric acids.

The concentration of starting compound in the carboxylic acid solvent is in no way critical being governed only by what is expedient. Advantageously, the compounds are present in acid solution in a concentration of from about 1 percent by weight to about 25 percent by weight.

The heavy metal oxidation catalyst can be used in its elemental finely divided form, or other combined forms. It has been found advantageous to employ the metals in the forms in which the metal ion itself is provided. Typical of the heavy metal catalysts are manganese acetate, cobalt acetate, nickel acetate, tin acetate, ammonium molybdate, cobalt hydroxy quinolate, and the like.

Preferred are the heavy metal acetates and particularly preferred is cobaltous acetate.

The amount of catalyst which is most efficacious can be easily determined by one skilled in the art. Advantageously, the catalyst is employed in an amount of from about 1 to about 20 mole percent based on moles of starting compound. Preferably, the catalyst is employed within a range of about 5 to about 15 mole percent.

Any of the known promoters for increasing the overall rate of an autoxidation reaction can be used in the present process. Typical, but not limiting thereof are methyl ethyl ketone, ozone, zirconyl acetate, sodium acetate, zinc acetate, sources of bromine such as hydrogen bromide, ammonium bromide, potassium bromate, tetrabromoethane, benzyl bromide, potassium bromide, sodium bromide, and the like. Preferred promoters are the compounds providing bromine, particularly ionic bromine, such as potassium bromide, sodium bromide, and combinations of these bromine providers with methyl ethyl ketone, and the like.

The amount of promoter can vary within wide limits. For example, it can be used in an amount of from about 1 to about 50 mole percent based on the moles of starting aromatic compound.

In most cases it is convenient to employ the catalyst and bromine providing promoters in equimolar proportions. When methyl ethyl ketone is additionally employed it can be used in any proportion, but, advantageously falls within the 1 to 50 mole percent range set forth above.

The oxygen gas can be employed in the form of pure oxygen, or admixed with other inert gases including the use of air itself. Preferably, pure oxygen is used at a sufficient pressure to maintain a blanket of the gas about the reaction mixture.

The autoxidation is advantageously carried out at a temperature of at least about 120° C. Preferably, the temperature is from about 130° C. to about 250° C.

The progress of the autoxidation can be followed using any convenient analytical technique such as thin layer chromatography (TLC), gas/liquid chromatography (GC), high pressure liquid chromatography (HPLC), and the like. TLC is a particularly useful means for following the course of the reaction and determining the termination thereof.

The time required to convert the starting benzophenone (I) to the dianhydride will depend on the boiling point of the carboxylic acid solvent (hence the reaction temperature), the particular catalyst and promoter combination, whether the autoxidation is carried out under normal or superatmospheric pressure conditions, and the like. Insofar as normal atmospheric pressure conditions are employed, the length of time for the autoxidation to be completed is controlled largely by the reaction temperature. In the event that lower temperatures are employed, for example 130° to 150° C., then, generally speaking, the autoxidation will be complete within a period falling within 20 to 72 hours. Obviously, when operating at higher reaction temperatures the time would be reduced accordingly.

The dianhydride products are easily isolated from the reaction mixtures and obtained in pure form by known methods. Illustratively, the acid solvent can be removed by distillation procedures providing the products in crude form. The pure materials can be removed from the catalyst and promoter by extraction with an organic solvent followed by solvent removal.

A particularly efficacious means of product isolation comprises cooling the reaction solution to about 0° C. thereby causing the dianhydrides to precipitate. The solid crystalline products are then isolated in high yields and a high state of purity simply by filtration methods and the like.

The novel bis(ortho dialkyl-phenoxy)benzophenones (I) for use in the present autoxidation method are prepared in high yields using the procedure known in the art as the Ullmann reaction and in accordance with the reaction scheme set forth in the following REACTION CHART. Specifically, the ortho dialkylphenol (IIIa), or (IIIb), or mixture thereof in the form of the phenoxide ion (formed from the interaction with a strong base MOH) is reacted in at least a two molar proportion with the dihalobenzophenone (IV) in an inert solvent in the presence of a copper catalyst to form (I) and the salt MX. A full description of typical Ullmann reaction conditions is taught in European Patent Application 51,235, May 12, 1982.

In respect of the phenols (IIIa) and (IIIb), R, $R_1$, $R_2$, and $R_3$ have the same significance as set forth above. It will be apparent to one skilled in the art that while in some cases the starting phenols can comprise mixtures of different phenols falling within the definitions of (IIIa) and (IIIb), in most cases, and preferably, the starting phenol will be a single species (IIIa) or (IIIb). The phenol is employed in substantial excess over the stoichiometric proportions and preferably up to 10 moles per mole of benzophenone (IV).

Illustrative of the phenols are 2,3-dimethylphenol, 3,4-dimethylphenol, 2,3-diethylphenol, 3,4-diethylphenol, 2,3-dipropylphenol, 3,4-dipropylphenol, 2,3-dibutylphenol, 3,4-dibutylphenol, 2,3-dipentylphenol, 3,4-dipentylphenol, 2,3-dihexylphenol, 3,4-dihexylphenol, 2,3-diheptylphenol, 3,4-diheptylphenol, 2,3-dioctylphenol, 3,4-dioctylphenol, and the like; 2-methyl-3-ethylphenol, 2-ethyl-3-methylphenol, 3-methyl-4-ethylphenol, 3-ethyl-4-methylphenol, and the like.

The halo group X in the benzophenone (IV) can be fluorine, chlorine, bromine, or iodine, preferably X is fluorine, chlorine or bromine. While it is not essential that both halo groups be symmetrically substituted in respect of each other, it is preferred that they be in the para-para' or ortho-ortho' relationship, and most preferably, para-para'.

Illustrative of the benzophenones are 4,4'-dichlorobenzophenone, 4,4'-dibromobenzophenone, 4,4'-diiodobenzophenone, 4,4'-difluorobenzophenone, 3,3'-dichlorobenzophenone, 3,3'-dibromobenzophenone, 2,2'-dichlorobenzophenone, 2,2'-dibromobenzophenone, and the like.

MOH represents a strong base and typically an alkali metal hydroxide such as lithium, sodium, or potassium, or any other strong base known in the art for replacing the phenolic hydrogen atom such as the conjugate cation of a quaternary ammonium hydroxide such as tetramethyl-, or tetraethyl-ammonium hydroxide and the like. The base can be employed in stoichiometric amounts in respect of the phenol, or, optionally and preferably, in less than stoichiometric amount.

In respect of the solvent which can be employed included is any inert solvent. The term "inert solvent" means any organic solvent which does not react with the reactants and product or otherwise interfere with the course of the reaction. Illustrative of organic solvents are benzene, toluene, xylene, glyme (dimethylether of ethylene glycol) diglyme (dimethylether of diethylene glycol), triglyme (dimethylether of triethyleneglycol), and the like.

The copper catalyst includes any of those copper compounds known to act as catalysts in the Ullmann reaction. Illustrative, but not limiting thereof are copper powder, copper chloride, copper carbonate, basic copper carbonate, copper (cupric) salts of the lower aliphatic carboxylic acids such as the acetates, propionates, and the like.

Preferred as catalysts are the copper carbonate, basic copper carbonate, cupric acetate, and cupric propionate. The optimum proportion of catalyst can be readily determined but, generally speaking, falls within a range of about 0.0001 to 5 mole percent based on the phenoxide.

The reaction temperature is advantageously from about 150° C. to about 225° C., and, preferably from about 170° C. to about 200° C. Time is not a critical factor and depends largely on the temperature of the reaction. Generally speaking, the reaction is completed within a period from about 0.5 hour to about 8 hours.

The bis(ortho dialkyl-phenoxy)benzophenones (I) are readily isolated from their reaction mixtures by first neutralizing the residual basicity using any desired acid either inorganic or organic. Preferably, the acid is inorganic such as dilute hydrochloric acid. The product is then separated as the organic portion from the aqueous acid and the salt MX.

Thereafter the benzophenone is isolated from the organic layer using conventional methods such as removal of the solvent by distillation followed by vacuum distillation of residual phenols and finally crystallization of the pure product.

While any of the novel bis(ortho dialkyl-phenoxy)-benzophenones can be autoxidized in accordance with the present method, preferred as a class are those wherein R, $R_1$, $R_2$, and $R_3$ are all methyl groups and those having the symmetrical configuration (Ia) set forth in the Formula Chart.

Illustrative but not limiting of the bis(ortho dialkyl-phenoxy)benzophenones in accordance with this invention are 4,4'-bis(2,3-dimethylphenoxy)benzophenone, 4,4'-bis(2,3-diethylphenoxy)benzophenone, 4,4'-bis(2,3-dibutylphenoxy)benzophenone, 4,4'-bis(3,4-dimethylphenoxy)benzophenone, 4,4'-bis(3,4-diethylphenoxy)benzophenone, 4,4'-bis(3,4-dibutylphenoxy)benzophenone, 4,4'-bis(3-methyl-4-ethylphenoxy)benzophenone, 3,3'-bis(2,3-dimethylphenoxy)benzophenone, 3,3'-bis(3,4-dimethylphenoxy)benzophenone, 2,2'-bis(3,4-dimethylphenoxy)benzophenone, and the like.

A preferred group of said benzophenones comprises 4,4'-bis(2,3-dimethylphenoxy)benzophenone, and 4,4'-bis(3,4-dimethylphenoxy)benzophenone.

The following examples describe the manner and process of making and using the invention and set forth the best mode contemplated by the inventor for carrying out the invention but are not to be construed as limiting.

EXAMPLE 1

The following experiment describes the preparation of 4,4'-bis(3,4-dimethylphenoxy)benzophenone in accordance with the present invention.

A four-necked 500 ml. flask provided with a thermometer, stirrer, reflux condenser, and Dean-Stark trap was charged with 98.0 g. (0.8 mole) of 3,4-dimethylphenol, 37.6 g. (0.15 mole) of 4,4'-dichlorobenzophenone, and 33.0 g. of 85 percent by weight potassium hydroxide (0.5 mole) in 100 ml. of xylene. Under a blanket of nitrogen during stirring, the reaction mixture was heated to reflux and the water formed (13 ml.) was collected from the trap over a period of about 2.5 hours. The removal of solvent was continued until the reaction mixture reached 190° C. (about 75 ml. of solvent was removed).

To the reaction mixture at 170° C. was added 0.4 g. of basic copper carbonate [$CuCO_3Cu(OH)_2$](1.2 mole percent based on the dichlorobenzophenone). The mixture was heated at 190° to 195° C. for 2 hours. The progress of the reaction was monitored by thin layer chromatography (TLC) of aliquot samples which were spotted on a silica gel plate (5 cm.×10 cm. KF5 plate supplied by Whatman Filter Co., Clifton, N.J.) and developed with a 20/1 by weight mixture of cyclohexane and ethyl acetate. The reaction was shown to be essentially over after 1 hour by the appearance of a single spot.

The mixture was cooled to 170° C. and diluted with 100 ml. of xylene. The solution was acidified with 20 ml. of concentrated hydrochloric acid in 100 ml. of water. After vigorously stirring for 30 minutes, the organic layer was separated, washed with warm water and dried over magnesium sulfate. The solvent was removed under reduced pressure (about 10 mm of mercury pressure) in a rotary evaporator. Then the residue was distilled to remove the unreacted 3,4-dimethylphenol, b.p.=below 100° C. (0.05 mm of mercury pressure). A residual oil was triturated with about 75 ml. of isopropanol at room temperature which resulted in the formation of a precipitate. The mixture of solid and isopropanol was cooled in ice for about 2.5 hours and the crystalline solid collected by suction filtration. The filter cake was washed with about 25 ml. of ice-cold isopropanol. After being dried in a vacuum oven at ambient 20° C. and 10 mm. of pressure there was obtained 60.0 g. (95% yield) of 4,4'-bis(3,4-dimethylphenoxy)benzophenone; m.p. 68 to 69° C.; with the following elemental analysis Calcd. for $C_{29}H_{26}O_3$: C, 82.43%; H, 6.22%;
Found: C, 82.41%; H, 6.25%.

EXAMPLE 2

The following experiment describes the preparation of 4,4'-bis(3,4-dicarboxyphenoxy)benzophenone dianhydride in accordance with the present invention.

A three-necked 100 ml. flask provided with a reflux condenser, a thermometer, a magnetic stirrer, and a gas inlet tube was charged with 4.2 g. (0.01 mole) of 4,4'-bis(3,4-dimethylphenoxy)benzophenone prepared in accordance with Example 1 above, 0.2 g. (0.001 mole) of cobaltous acetate tetrahydrate [10 mole percent based on the benzophenone substrate], 0.1 g. (0.001 mole) of sodium bromide, 0.25 g. of methyl ethyl ketone, and 50 ml. of propionic acid. The reactants were stirred and heated at 134° to 135° C. using an oil bath set to cycle at 175° to 180° C. A stream of oxygen was bubbled into the stirred solution through a diffuser using an Ace Glass flowmeter (4-15-2) set at a flow rate of about 50 ml. per minute. The gas was passed through the stirred solution at the above specified temperature for 24 hours. An aliquot sample was removed for TLC analysis and when spotted on a K5F silica gel plate and developed with a 50/1 by weight mixture of ethyl acetate and acetic acid showed the presence of only one component.

The reaction mixture was cooled in ice water causing the crystallization of a solid. The solid was collected by suction filtration, washed with cold propionic acid, then dried at 100° C. under 10 mm. of mercury pressure for 6 hours. Thus, there was obtained 4.2 g. (83% yield) of 4,4'-bis(3,4-dicarboxyphenoxy)benzophenone dianhydride; m.p. 208 to 210° C.; typical infrared absorption at 1850 cm$^{-1}$ for an anhydride and with the following elemental analysis Calcd. for $C_{29}H_{14}O_9$: C, 68.78%; H, 2.79%
Found: C, 68.40%; H, 3.07%.

FORMULA CHART

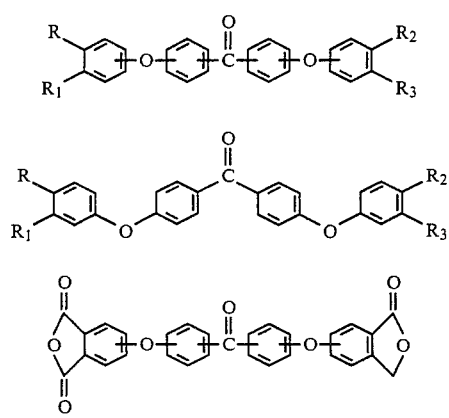

REACTION CHART

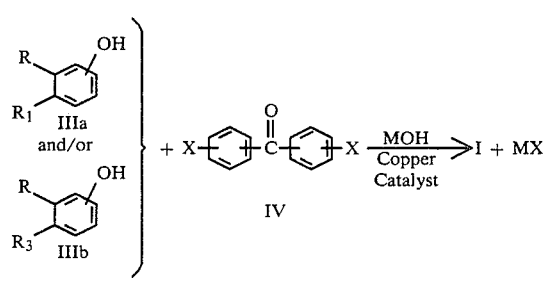

I claim:

1. A method for converting a bis(ortho dialkylphenoxy)benzophenone having the formula (I)

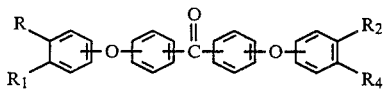

to the corresponding dianhydride having the formula (II)

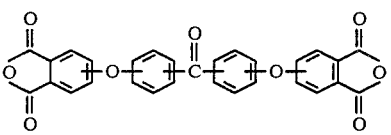

wherein R, $R_1$, $R_2$, and $R_3$ are independently selected from linear lower alkyl, said method comprising autoxidizing said benzophenone (I) in a solution of an aliphatic monocarboxylic acid having 3 to 8 carbon atoms with oxygen in the presence of a heavy metal oxidation catalyst and a promoter and at a temperature of at least about 120° C. to form said dianhydride (II).

2. A method according to claim 1 wherein said monocarboxylic acid is propionic acid.

3. A method according to claim 1 wherein said catalyst and promoter are cobaltous acetate and sodium bromide respectively.

4. A method according to claim 3 wherein methyl ethyl ketone is employed as an additional promoter.

5. A method according to claim 1 wherein said autoxidation is carried out at a temperature of from about 130° C. to about 250° C.

6. A method according to claim 1 wherein said benzophenone (I) has the formula

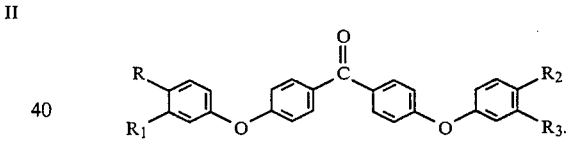

7. A method according to claim 1 wherein R, $R_1$, $R_2$, and $R_3$ are all methyl groups.

8. A method according to claim 1 wherein 4,4'-bis(3,4-dimethylphenoxy)benzophenone is converted to 4,4'-bis(3,4-dicarboxyphenoxy)benzophenone dianhydride.

9. A method for converting 4,4'-bis(3,4-dimethylphenoxy)benzophenone to 4,4'-bis(3,4-dicarboxyphenoxy)benzophenone dianhydride comprising autoxidizing said starting benzophenone in a solution of propionic acid with oxygen in the presence of cobaltous acetate as catalyst and a promoter combination of sodium bromide and methyl ethyl ketone at a temperature of from about 130° C. to about 250° C.

* * * * *

UNITED STATES PATENT AND TRADEMARK OFFICE
CERTIFICATE OF CORRECTION

PATENT NO. : 4,577,034

DATED : March 18, 1986

INVENTOR(S) : Visweswara R. Durvasula

It is certified that error appears in the above-identified patent and that said Letters Patent is hereby corrected as shown below:

Column 1, lines 44 and 45 "descibed" should read
-- described --. Column 3, line 23 "thereof" should read
-- thereof, --. Column 7, FORMULA CHART, Formula II, line 40, that portion of the formula reading

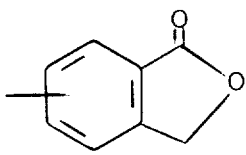   should read   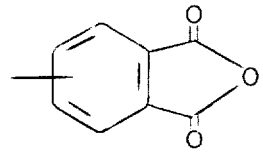

Column 7, REACTION CHART, Formula IIIb, line 52, that portion of the formula reading

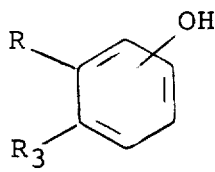   should read   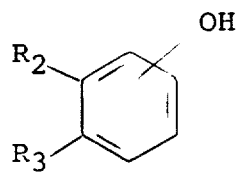

UNITED STATES PATENT AND TRADEMARK OFFICE
CERTIFICATE OF CORRECTION

PATENT NO. : 4,577,034
DATED : March 18, 1986
INVENTOR(S) : Visweswara R. Durvasula It is certified that error appears in the above-identified patent and that said Letters Patent is hereby corrected as shown below:

Column 8, Claim 1, line 7, that portion of the formula reading

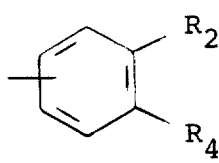   should read   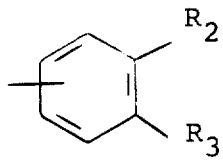

Signed and Sealed this

Third Day of February, 1987

Attest:

DONALD J. QUIGG

Attesting Officer

Commissioner of Patents and Trademarks